US00PP26415P2

(12) United States Plant Patent
Carmen

(10) Patent No.: US PP26,415 P2
(45) Date of Patent: Feb. 16, 2016

(54) ***WISTERIA* PLANT NAMED 'ED'S BLUE DRAGON'**

(50) Latin Name: *Wisteria floribunda*
Varietal Denomination: Ed's Blue Dragon

(71) Applicant: Paul Turner, Hobsonville, Auckland (NZ)

(72) Inventor: Ed Carmen, Gilroy, CA (US)

(73) Assignee: Paul Turner, Auckland (NZ)

( * ) Notice: Subject to any disclaimer, the term of this patent is extended or adjusted under 35 U.S.C. 154(b) by 320 days.

(21) Appl. No.: 13/986,570

(22) Filed: May 15, 2013

Related U.S. Application Data

(60) Provisional application No. 61/688,582, filed on May 17, 2012.

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

(56) References Cited

PUBLICATIONS http://carmansnursery.com/docs/articles/o_a_2011_june_edsbluedragon.pdf; 2 pages; Jun. 2011.*

* cited by examiner

*Primary Examiner* — Kent L Bell
(74) *Attorney, Agent, or Firm* — Penny J. Aguirre

(57) ABSTRACT

A new cultivar of *Wisteria floribunda* named 'Ed's Blue Dragon', characterized by its double pale blue and mauve flowers and its vigorous growth rate with ease of propagation.

2 Drawing Sheets

Botanical classification: *Wisteria floribunda*.
Cultivar designation: 'Ed's Blue Dragon'.

BACKGROUND OF THE INVENTION

The present invention relates to a new and distinct cultivar of *Wisteria* plant, botanically known as *Wisteria floribunda* 'Ed's Blue Dragon' and will be referred to hereafter by its cultivar name, 'Ed's Blue Dragon'. The new cultivar represents a new Japanese *wisteria* grown as a vine or shrub for landscape use.

'Ed's Blue Dragon' arose from a breeding project conducted by the Inventor in Los Gatos, Calif. Pollen from various unnamed plants in the Inventors breeding program was used to pollinate plants of 'Black Dragon' (not patented) and the resulting seeds pooled and sowed. The male parent is therefore unknown. 'Ed's Blue Dragon' was selected as a single unique plant in spring of 1996 from amongst the resulting seedlings.

Asexual reproduction of the new cultivar was first accomplished by grafting in Los Gatos, Calif. by the Inventor in 1997. Asexual reproduction by grafting and stem cuttings has determined that the characteristics of this cultivar to be stable and reproduced true to type in successive generations.

SUMMARY OF THE INVENTION

The following traits have been repeatedly observed and represent the characteristics of the new cultivar. These attributes in combination distinguish 'Ed's Blue Dragon' as a unique cultivar of *Wisteria*.

1. 'Ed's Blue Dragon' exhibits double flowers.
2. 'Ed's Blue Dragon' exhibits flowers that are pale blue and mauve in color.

3. 'Ed's Blue Dragon' has a vigorous growth habit and is readily propagated by grafting and stem cuttings.

'Black Dragon', the female parent, differs from 'Ed's Blue Dragon' in having dark purple-mauve colored double flowers. 'Black Dragon' is grown under many synonym names: 'Violacea Plena', 'Yae Koku Riu', 'Multijuga Flore Fleno', and 'Longissima Plena', and 'Yae Fuji'. 'Ed's Blue Dragon' can also be compared to the cultivar 'Domino' (not patented), which differs from 'Ed's Blue Dragon' in having single rosette shaped flowers that are mauve-blue in color.

BRIEF DESCRIPTION OF THE DRAWINGS

The accompanying colored photographs illustrate the overall appearance and distinct characteristics of the new *Wisteria*. The photographs were plants about 4 years in age as grown outdoors in open ground in Taranaki, New Zealand.

The photograph in FIG. 1 is a view of inflorescences of 'Ed's Blue Dragon'.

Figure 1:
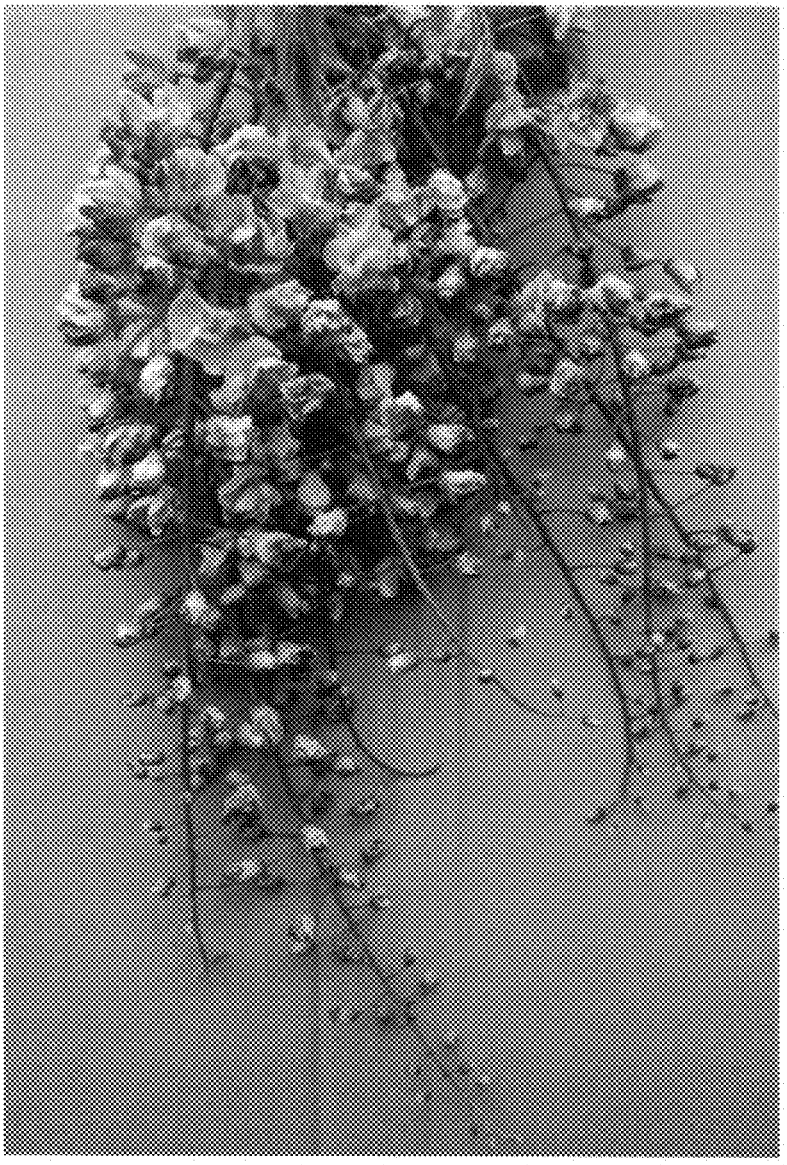
Figure 2:
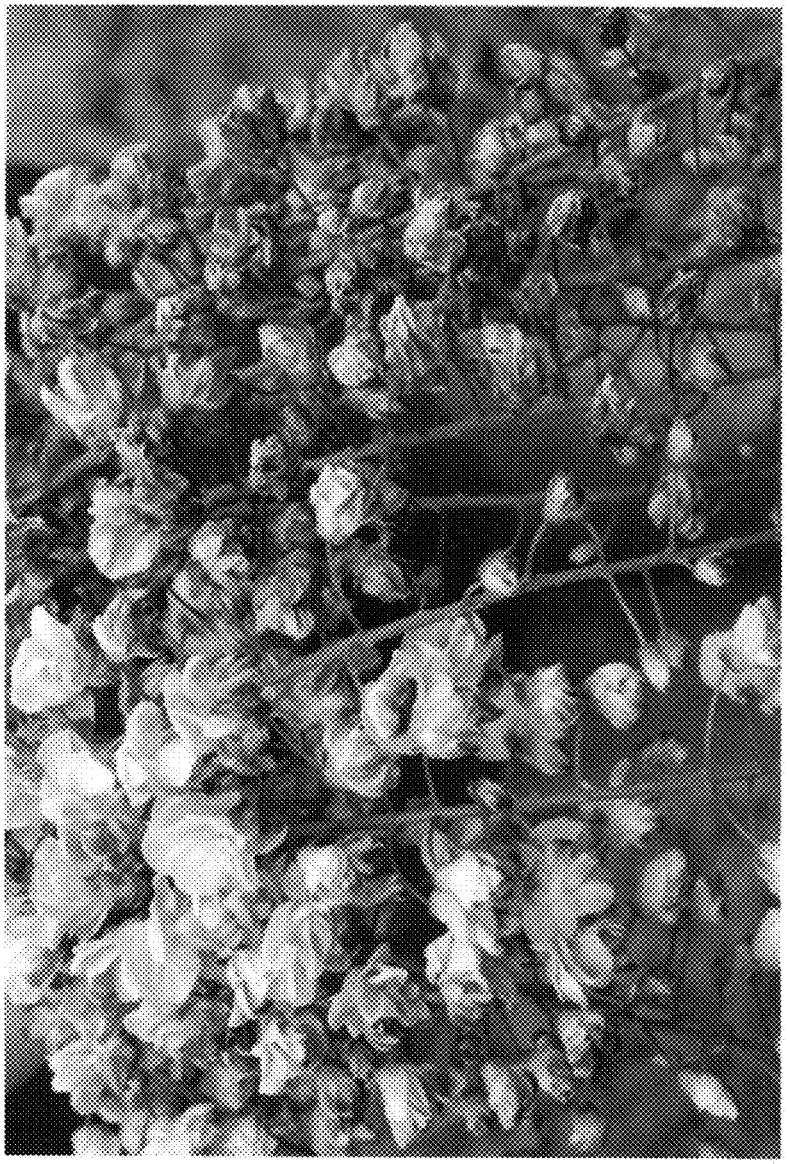

The photograph in FIG. 2 is of a close-up view of the flowers of 'Ed's Blue Dragon' (bottom) in comparison to the flowers of 'Black Dragon' (top).

The colors in the photographs are as close as possible with the digital photography and printing techniques utilized and the color codes in the detailed botanical description accurately describe the colors of the new *Wisteria*.

DETAILED BOTANICAL DESCRIPTION OF THE PLANT

The following is a detailed description of plants about 4 years in age as grown outdoors in open ground in Taranaki, New Zealand. Plants were grown under average day temperatures of 18 to 20° C. and average night temperatures of 10 to 15° C. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—4 to 5 weeks in mid to late spring in New Zealand.

*Plant type.*—Deciduous woody vine.

*Plant habit.*—Climbing vine.

*Height.*—Length is indeterminate, will grow to 2 m in height before spreading outward as a vine if free-standing (unsupported).

*Hardiness.*—U.S.D.A. Zones 4 to 9.

*Diseases and pests.*—No susceptibility or resistance to diseases or pests has been observed.

*Root description.*—Fleshy main roots with fine roots developing after 4 to 5 months.

Growth and propagation:

*Propagation.*—Hardwood cuttings or grafting.

*Rooting.*—Hardwood cuttings placed in heated sawdust will callus in 10 to 20 days, cuttings are placed in a prepared soil bed through black plastic and under a protective glass dome cloches with soil temperatures of 12 to 15° C. and roots appear in 15 to 20 days.

*Growth rate.*—Vigorous.

Stem description:

*Branch habit.*—Basal with an average of 10 lateral branches per basal stem.

*Stem diameter.*—Young stems average 4 mm, mature secondary branches average 1 to 2 cm.

*Stem shape.*—Round.

*Stem aspect.*—Upright and becoming either procumbent or climbing.

*Stem color.*—Young stems 146C speckled with 166B, mature bark 199D and speckled with 166B and occasional longitudinal stripes of 156C.

*Stem surface.*—Glabrous when young, smooth but bark-like (ridged) when mature.

*Stem internode length.*—Variable; ranging from 7 to 20 cm.

Foliage description:

*Leaves.*—Ovate in overall outline, division is odd pinnate; 11 to 13 leaflets, arrangement is initially in whorls becoming alternate, average of 40 cm in length and 15.5 cm in width when mature, 20 to 4.0 per lateral branch.

*Leaflets.*—Ovate in shape, rounded base, acute apex, venation; pinnate pattern, conspicuous but not prominent, 137B on upper surface and 137D on lower surface, entire and undulate margins, petiolate attachment, opposite arrangement, surface; glabrous on upper surface and lower surface and slightly bullate, color when expanding on upper surface; 146C, color when expanding on lower surface; 146D, color when mature; upper surface 137B and lower surface 137D, size; 55 to 10 cm in length, 3 to 4.5 cm in width (terminal leaves the largest).

*Petioles.*—3 to 6 cm in length and 1.5 mm in width, 144A in color, surface is glabrous.

*Petiolules.*—3 to 4 mm in length and 1.5 mm in width, 144A in color, surface is glabrous.

*Rachis.*—Average on 3 cm in length and 1.5 mm in width on mature leaves, 144A in color, surface is glabrous.

*Stipules.*—Not present.

Flower description:

*Inflorescence type.*—Terminal and auxiliary racemes of double flowers, blooms from the base to the apex, cascading.

*Inflorescence size.*—35 to 40 cm in length, tapering from 8 to 12 cm in width down to 2 cm in width.

*Inflorescence quantity.*—1 to 10 per stem.

*Lastingness of inflorescence.*—3 to 4 weeks (opens from base to apex).

*Flower size.*—About 2 cm in depth and 2 to 3.5 cm in diameter.

*Flower number.*—About 40 per inflorescence.

*Flower fragrance.*—Mild.

*Peduncle.*—Oval in shape, up to 40 cm in length and 2 to 3 mm in width, 139C in color, glabrous surface with some nodules, flowers are arranged irregularly (both apposite and alternate), internode length is an average of 1.5 cm.

*Petiole.*—3 to 5 cm in length and 1 mm in width, oval in shape, 147B in color, glabrous surface, held nearly horizontal to peduncle.

*Flower buds.*—Round in shaped, 1 to 1.5 cm in length and 9 mm in width prior to opening, color a blend of 104B and 92B.

*Flower type.*—Irregular but campanulate-like, held nearly horizontal to stem.

*Calyx.*—Campanulate, sepals fused at base.

*Sepals.*—3 to 4 mm in length and 1 to 2 mm in diameter, margin entire, acute apex, fused base, color is 147C and blending to 147A at base, surface on upper and lower surface is slightly pubescent.

*Corolla features.*—About 20 petals and petaloids, round in shape, 2 to 3 cm in length and 0.5 to 1 cm in diameter, rounded apex, rounded base, upper surface and lower surface is glabrous, color when opening upper and lower surface; 106D and suffused with 104B and 92B, color when fully open upper and lower surface; 106D, color fades on upper and lower surface; 108D.

Reproductive organs:

*Gynoecium.*—1 Pistil, stigma; rounded with small tip, 147B in color. Pistil. — 1.4 cm in length, 1 mm in width; style is horizontal to ovary, 0.3 mm in width, 8 mm in length and 144D in color; stigma as above is okay, ovary is superior, hairy surface, 144B in color, 9 mm in length and 1 mm in width; stipe is 144D in color, 2 mm in length and 1 mm in width.

*Androecium.*—No stamens present.

*Fruit and seed.*—Seeds were not observed to be produced.

It is claimed:

1. A new and distinct cultivar of *Wisteria* plant named 'Ed's Blue Dragon' as herein illustrated and described.

* * * * *